US 6,696,679 B1

(12) United States Patent
Graef et al.

(10) Patent No.: US 6,696,679 B1
(45) Date of Patent: Feb. 24, 2004

(54) METHOD FOR FOCUSING OF DISK-SHAPED OBJECTS WITH PATTERNED SURFACES DURING IMAGING

(75) Inventors: Michael Graef, Jena (DE); Uwe Graf, Solms (DE); Joachim Wienecke, Jena (DE); Guenter Hoffmann, Jena (DE); Karl-Heinz Franke, Ilmenau (DE); Lutz Jakob, Jena (DE)

(73) Assignee: Leica Microsystems Wetzlar GmbH, Wetzlar (DE)

( * ) Notice: Subject to any disclaimer, the term of this patent is extended or adjusted under 35 U.S.C. 154(b) by 0 days.

(21) Appl. No.: 09/446,463

(22) PCT Filed: Jun. 24, 1998

(86) PCT No.: PCT/DE98/01726

§ 371 (c)(1),
(2), (4) Date: Apr. 12, 2000

(87) PCT Pub. No.: WO98/59235

PCT Pub. Date: Dec. 30, 1998

(30) Foreign Application Priority Data

Jun. 24, 1997 (DE) .......................................... 197 26 696

(51) Int. Cl.$^7$ ............................................... G02B 27/40
(52) U.S. Cl. ............................. 250/201.4; 250/559.45; 356/237.4; 348/126
(58) Field of Search ...................... 250/201.2–201.9, 250/559.04, 559.05, 559.46, 559.39, 559.42, 559.45; 356/237.4, 237.5; 382/145, 204; 348/125, 126

(56) References Cited

U.S. PATENT DOCUMENTS

| 4,203,031 A | | 5/1980 | Kamachi et al. ............ 250/201 |
| 4,577,095 A | * | 3/1986 | Watanabe ................ 250/201.2 |
| 4,740,079 A | * | 4/1988 | Koizumi et al. ........ 250/559.41 |
| 4,833,315 A | * | 5/1989 | Horikawa ................ 250/201.7 |
| 4,902,101 A | | 2/1990 | Fujihara et al. ............. 350/320 |
| 5,365,051 A | * | 11/1994 | Suzuki et al. ............ 250/201.2 |
| 5,483,056 A | * | 1/1996 | Imai ........................ 250/201.4 |
| 5,808,735 A | * | 9/1998 | Lee et al. ............... 250/559.42 |
| 5,960,107 A | * | 9/1999 | Leroux ........................ 382/145 |
| 6,043,475 A | * | 3/2000 | Shimada et al. ......... 250/201.3 |
| 6,444,967 B1 | * | 9/2002 | Kosuge et al. ........... 250/201.3 |

FOREIGN PATENT DOCUMENTS

| DE | 37 35 091 | | 4/1988 |
| DE | 280 840 | | 7/1990 |
| DE | 44 10 603 | | 6/1995 |
| JP | 41-42055 | * | 5/1992 |
| WO | 95/19552 | | 7/1995 |

OTHER PUBLICATIONS

Patent Abstracts of Japan, "Inspecting Apparatus for Appearance of Semiconductor Wafer", JP 41–42055, (May 15, 1992), Abstract of Sato Kenji, Appln. No. 22–64434, (Oct. 1, 1990).

Itoh, Kazuyoshi et al., "Applied Optics, vol. 28, No. 15", *Digitized optical microscopy with extended depth of field*, pp. 3487–3493, (Aug. 15, 1989).

* cited by examiner

*Primary Examiner*—Stephone B. Allen
(74) *Attorney, Agent, or Firm*—Foley & Lardner

(57) ABSTRACT

A method for focusing on disk-shaped objects with patterned and unpatterned surfaces includes imaging of the patterned and unpatterned surfaces on a disk-shaped object for defect detection and defect classification by using various preset values of a focus regulation system to acquire the image sequence. At least one preset value is learned on the basis of an image sequence at least at one position in a substantially flat reference region of the surface of the disk-shaped object. A regulated adjustment is provided of a measurable distance from a carrier plane to a reference plane, wherein the carrier plane serves as a support for the disk-shaped objects. The distance is adjusted by applying the at least one preset value, which is overlaid on the regulation system, a focus state is evaluated by an image processor according to at least one rule, and the at least one preset value is ascertained therefrom.

9 Claims, 4 Drawing Sheets

METHOD FOR FOCUSING OF DISK-SHAPED OBJECTS WITH PATTERNED SURFACES DURING IMAGING

FIELD OF THE INVENTION

The invention concerns a method for focusing of disk-shaped objects having patterned surfaces. This is done by regulated adjustment of the measurable distance from a carrier plane serving as support for the objects to a reference plane.

The method is applicable predominantly to process inspection of semiconductor wafers during the manufacturing process.

The purpose of an inspection during the manufacture of integrated circuits is to scan both unpatterned and patterned semiconductor wafers one image field at a time, to detect defects that are present, and lastly to assign them to defect groups by classification.

BACKGROUND OF THE INVENTION

DE 44 10 603 C1 has disclosed a method that is the basis for the recognition of defects (specific image point features) of an image acquired of the surface of the semiconductor wafer. Direct defect detection of this kind on the basis of natural distinguishing features between background and defect and the typical properties of various types of defects can, in contrast to reference/actual comparison, largely dispense with comprehensive information about the reference pattern, since it proceeds from specific basic rules and rule deviations in the context of image recognition. Rules and rule deviations of this kind are defined substantially by geometrical and color features of the reference pattern or reference layer, and of the defect.

It is a characteristic of the method that an intermediate image generated by image point classification contains image point features as probabilities (converted into gray values) of membership in regions that have become known by training, including the gray value scales of transitions between adjacent regions.

For the analysis of image contents using the basic idea of process inspection and quality control, it is particularly interesting to know how and with what quality the patterns and defects are being imaged as three-dimensional structures with the aid of optical systems.

Since the actual appearance of patterns and defects of the surface of the semiconductor wafer depicted in the image changes as a function of the focus state, the setting of that focus state is extraordinarily important.

Known optical methods for analyzing a focus state have the disadvantage of not satisfactorily dealing with large reflectance fluctuations over smaller and larger areas of the semiconductor wafer, or with further influencing factors such as wedge errors, roughness, ripple, or fluctuations in pattern height in the image field which in some cases are greater than the depth of field. In the analysis result, for example, reflectance fluctuations simulate nonexistent height fluctuations or stage running errors that supposedly need to be controlled out.

Image point classification in the form of color classification is performed according to the method as defined in DE 44 10 603 C1. The method is based on the fact that color valences belong to undisturbed pattern components and can be estimated by sample analysis. The image point classification can be described in terms of their statistics by ellipsoidal clusters in the color space. The image points suspected of being defective yield defect clusters located outside the cluster and the separation of the defect clusters from the clusters of undisturbed patterns is considerably disrupted.

The consequence is an increase in the pseudo-defect rate and a decrease in recognition accuracy. Pseudo-defects are phenomena in the final inspection presentation that are mistakenly recognized by the inspection system as defects on the basis of their properties.

SUMMARY OF THE INVENTION

It is the object of the invention to make available to the image processor images that result in an increase in the accuracy with which defects are recognized, so that defect recognition becomes more reliable.

According to the present invention, the object is achieved by a method for focusing during the imaging of patterned surfaces of disk-shaped objects, by regulated adjustment of the measurable distance from a carrier plane serving as support for the objects to a reference plane, in that:

the distance established by regulated adjustment is corrected by an unregulated preset value to be utilized at least for a subregion of the surface.

The preset value valid for a subregion is ascertained on the basis of an image sequence, for at least one position in a substantially flat reference region of the surface, which is acquired using various preset values of the focus regulation system. The quality of the focus state is evaluated in accordance with at least one rule.

In a first embodiment, the preset value belonging to the highest-contrast image determined by image processing is used to establish a corrected distance.

In a second embodiment, the preset value belonging to the image having a minimum number of defects is used to establish a corrected distance.

In a third embodiment, the preset value belonging to the image having a minimum number of defect pixels in proportion to the total defect area. The present value is used to establish a corrected distance.

Lastly, in a fourth embodiment, the preset value belonging to the image having a minimum number of pseudo-defect pixels is used to establish a corrected distance.

The reference region is selected based on the lowest gradient of the height profile of the surface, which is to be determined by ascertaining the values of the distance from the carrier plane to the reference plane, at locations of repeating height marks, for the preset value of the focus regulation system at which at least one rule is adhered to.

During inspection in the form of a defect search one image field at a time, the preset value of the focus regulation system ascertained for the image field position is used for focusing.

For defect classification, in which an image that contains a defect to be classified is compared to a reference image, acquisition of the reference image is performed with the corrected distance from carrier plane to reference plane ascertained for the reference image position.

To acquire the image with the defects to be classified, the value of the distance from carrier plane to reference plane used for focus setting is the one belonging to the highest-contrast image of a series of images with the defect to be classified, for which the preset value of the focus regulation system ascertained for the associated image position is varied in steps.

The invention thus provides, as the basis for focus setting, at least one preset value which is determined by training on the basis of reference regions and rules directed toward the result.

The result of an adaptive control system is principally that specific properties of the object are taken into account in focusing for purposes of defect recognition and classification. In addition, instrumental influences having a disruptive effect on focusing are eliminated.

BRIEF DESCRIPTION OF THE DRAWINGS

The invention will be explained below in more detail with reference to the schematic drawings, in which.

DETAILED DESCRIPTION OF THE INVENTION

Figure 1:
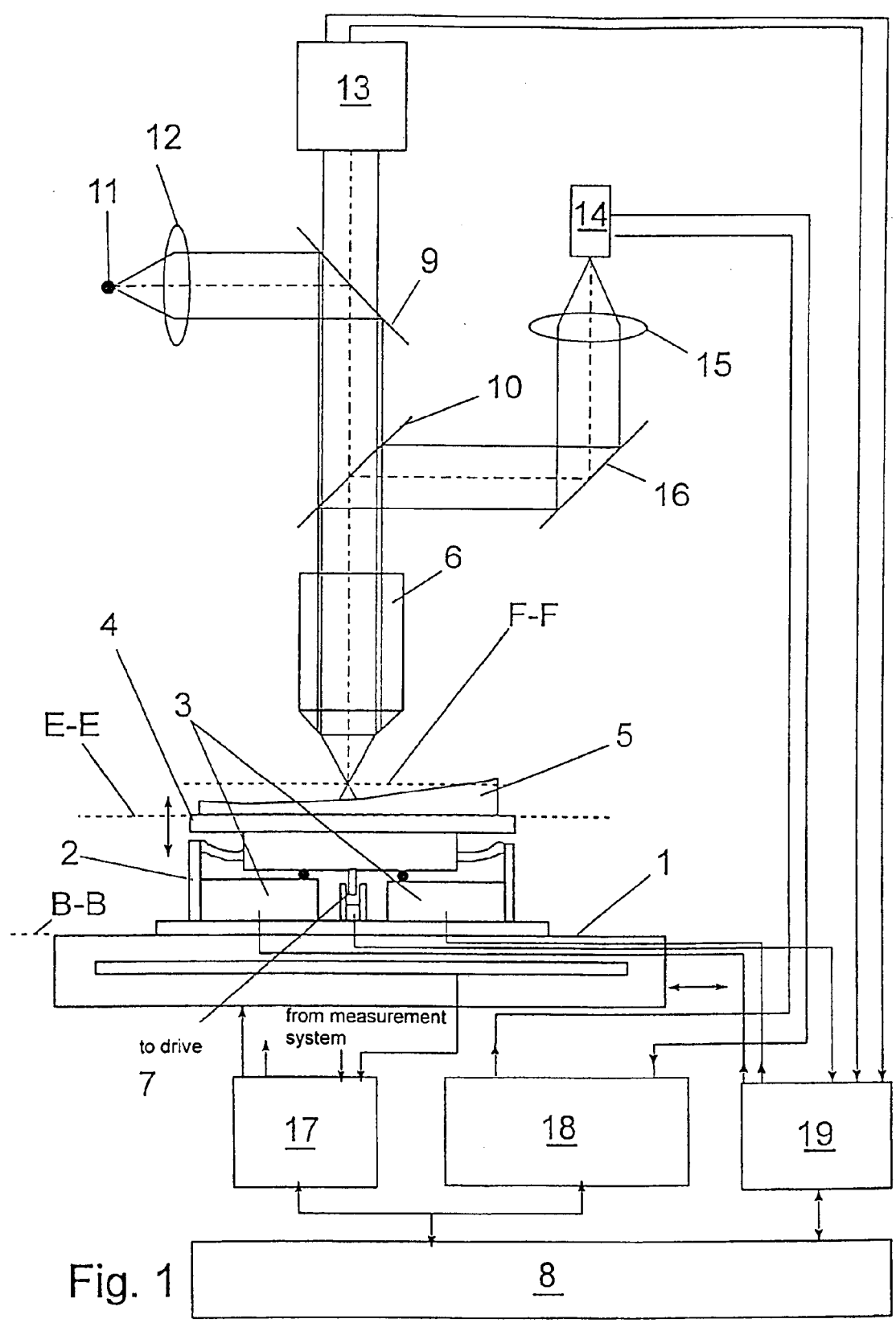
FIG. 1 shows a device for focusing during the imaging of patterned surfaces.

In the device depicted in FIG. 1 for focusing during the imaging of patterned surfaces, a wafer stage designed as an X-Y stage, of which only the portion displaceable in the X direction is depicted, carries a focus setting system 2. By way of piezoelements 3, a carrier 4 for reception of a disk-shaped object 5, for example a wafer, is displaceable with respect to focal plane F—F of a microscope objective 6 in a vertical direction for focusing purposes.

The relative displacement of carrier plate E—E with respect to focal plane F—F can be ascertained with an inductive measurement system 7 by measuring the distance to the stage surface serving as reference plane B—B.

Inductive measurement system 7, as an indicator control system, is also suitable for implementing the vertical position of carrier plane E—E as setpoint, the setpoint being defined by a device control and regulation system 8 in the context of the focusing method according to the present invention (yet to be described).

A light source 11 is coupled via an illuminating optical system 12, a focus measurement system 13, and a CCD measurement system 14 into the beam path of microscope objective 6 by way of semitransparent deflection mirrors 9, 10. CCD measurement system 14 additionally has an imaging tube system 15 and a deflection mirror 16 in its beam path.

A stage activation system 17, an image processor and camera activation system 18, and a focus regulation system 19 are connected to the central device control and regulation system 8.

X and Y measurement systems (not depicted) are connected to the inputs of stage activation system 17. The outputs of stage activation system 17 lead to X and Y drives (also not depicted) for wafer stage 1.

Input and outputs of image processor and camera activation system 18 are connected to CCD measurement system 14.

Whereas focus measurement system 13 and inductive measurement system 7 are connected to the inputs of focus regulation system 19, focus setting system 2 is coupled to the outputs.

Device control and regulation system 8 predefines a movement and operating regime pertinent to the wafer inspection.

Stage activation system 17 and the X and Y drives cause wafer table 1 to be moved in stepping mode into the requisite positions, the X and Y measurement systems signaling the fact that the intended position has been reached. Microscope objective 6 and tube system 15 image the wafer surface onto CCD measurement system 14. An image is acquired via image processor and camera activation system 18.

A focus state that guarantees analyzable images is produced by way of a focusing system that comprises focus measurement system 13, focus setting system 2, and focus regulating system 19.

Light source 11, configured as an LED, radiates in the near infrared region at approx. 870 nm, for clear separation from the "measurement light" of the defect inspection system (not depicted). To avoid stray light effects, the LED is also cycled at approx. 3.3 kHz.

The focusing system operates in accordance with a measurement principle in which a test object image is imaged by microscope objective 6 onto the surface to be focused. Intensity differences, resulting from a telecentric return image that is generally offset with respect to an identical reference test object, are sensed in two separate channels by two photodiodes and then analyzed. A focused state has been reached when the intensity difference is zero.

To achieve this state, the photodiode currents corresponding to the intensities are converted into voltage signals, amplified, conveyed to focus regulation system 19, and digitized. A control algorithm calculates a high-voltage adjusting value to be output, which is transferred as an analog signal to focus setting system 2 for vertical displacement of carrier 4.

The feature whereby the measured intensity difference is additively overlain by a digital value, identified in a specific manner, in the form of an offset or preset value is for variable utilization of the focusing system.

To ensure that the control algorithm nevertheless operates as a zeroing control system, carrier 4 with object 5 must be displaced vertically to such an extent that the intensity difference measured with focus measurement system 13 and digitized is of exactly the same magnitude the defined offset, but has the opposite sign.

According to the invention, it is thus possible by way of the offset on the one hand to adapt the regulation system plane to the actual focal plane F—F, while on the other hand deliberate departures from that plane can be established.

What is essential is that the Z position of object 5 established by way of the offset is still a regulated position, since wafer topologies are still being stabilized. Essentially, a parallel shift of the real object surface is accomplished.

Depending on the position of the X-Y table, a specific value of the offset can thus result in different values of inductive measurement system 7, since the latter uses the stage surface as reference plate B—B.

The focusing system operates even during displacement of object 5 from one position to the next. Measurement signals, to which focus regulation system 19 and focus setting system 2 continually react, are generated in quick succession (at least every 40 ms).

Particularly significant for the present invention is the use of CCD measurement system 14 in combination with image processor and camera activation system 18 to identify the focus states established with the focusing system, by calculating, using a contrast function of a contrast program known per se, the highest-contrast and therefore sharpest image from an image sequence.

An adaptation of the focusing system that is essential for carrying out the method according to the present invention is provided by a procedure which determines the preset values for the focus regulation system that minimize the pseudo-defect rate as stated in the presentation of the object. Rules based on the effects of various degrees of defocusing are used.

Optimum focus (FIG. 2a), at a focus position $f_{n0}$, means that defects are optimally detected.

A defect $F_0$ (count=$n_0$) with a total defect area $A_0$ is present in the image field depicted, which is divided into individual pixels $P_i$. In the present ideal situation, pseudo-defects $P_{F0}$ are not present.

Figure 2A:
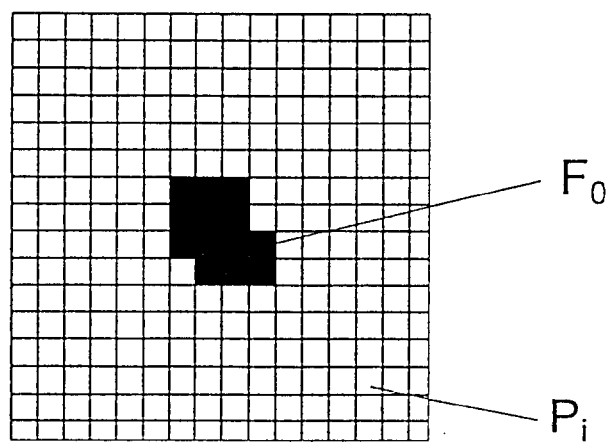
FIGS. 2a–2c show binary images of image fields of a defect region that are acquired with various focus settings.
Figure 2B:
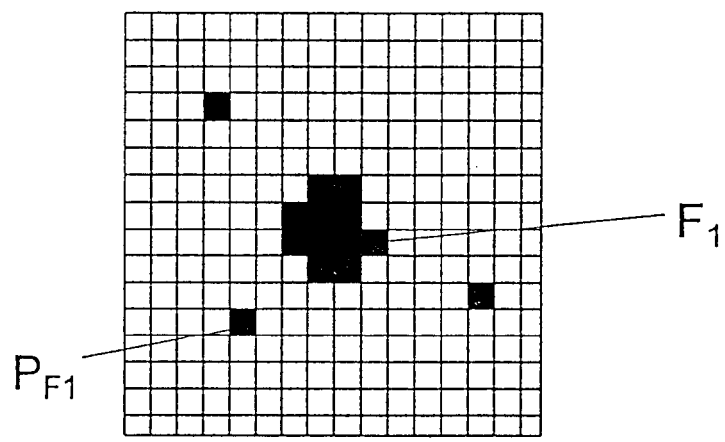

With a slight defocusing $F_{n1}$ (FIG. 2b), the defect count rises to $n_1 > n_0$ as compared to FIG. 2a due to the occurrence of first pseudo-defects $P_{F1}$. The actual defect $F_1$ becomes smaller, but the total defect area $A_1 > A_0$ increases due to the larger number of pseudo-defects. The number of defect pixels $P_1 > P_0$ rises.

Figure 2C:
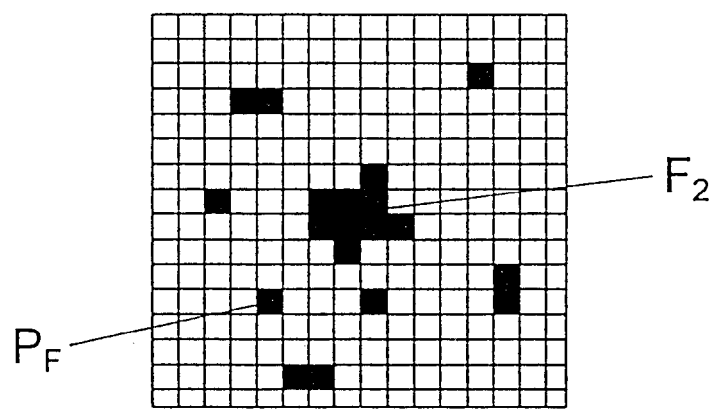

With severe defocusing $F_{n2}$ (FIG. 2c), the number and size of pseudo-defects $P_F$ rise, and there is also a definite increase in total defect area $A_2 > A_1$.

The defect count rises to $n_2 > n_1$, and the number of defect pixels to $P_2 > P_1$.

For rule application, with the X-Y stage in the neutral position, an image series of "n" images, each with a preset value for the focus regulation system modified by a value "m", is acquired from the wafer surface, then binarized, stored, and processed using corresponding image processing algorithms. The binary image contains the corresponding defect and the pseudo-defects. These images of the image series are used to ascertain the optimum focus and thus the optimum preset value.

The selected image is used for detection and classification of the defect.

Figure 3:
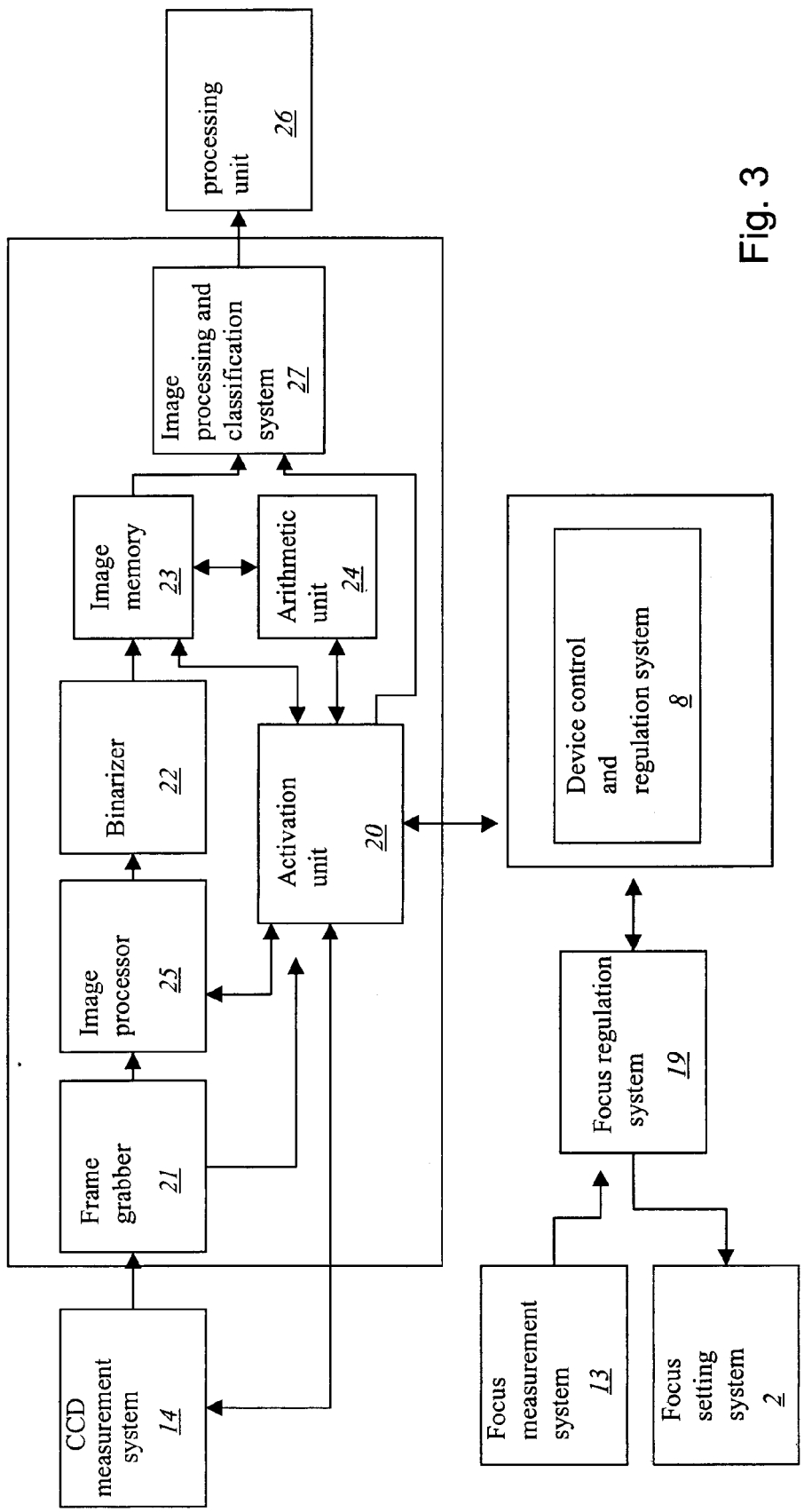
FIG. 3 shows the image processing unit and camera activation system in a block diagram.

This procedure is performed by using a configuration for image processor and camera activation system 18 as shown in FIG. 3.

Similarly to FIG. 1, image processor and camera activation system 18 is connected on the input and output side to device control and regulation system 8, from which an input-side and output-side connection to focus regulation system 19 also exists. Focus regulation system 19 is supplied with data from focus measurement system 13 with which focus setting system 2 can be controllably activated.

In image processor and camera activation system 18, an activation unit 20 is connected on the input and output side to a CCD measurement system 14, a frame grabber 21, a binarizer 22, an image memory 23, and an arithmetic unit 24. Activation unit 20 is coupled at a further output to a unit for image processing and classification 27 that also possesses access to image memory 23. A connection chain also exists from CCD measurement system 14 via frame grabber 21 and binarizer 22 to image memory 23.

It is advantageous to arrange, between frame grabber 21 and binarizer 22, further image processing components 25 for image improvement, noise suppression, and defect recognition.

According to a first of the rules to be utilized, the number of defects in the image is to be brought to a minimum.

A check is made in arithmetic unit 24 by counting the defects, in a manner familiar to one skilled in the art, in each of the binary images stored in image memory 23. Each time a defect is recognized, the counter is incremented by, for example, one unit. The image with the minimum number of defects is selected.

Activation unit 20 causes this image to be transferred to image processor/classification system 27, in which a classification of the defects present in the image field, in terms of their color, pattern, and shape, is performed according to known rules using a classifier.

The classified defects are collected in a processing unit 26 and stored, and are available for display after completion of the inspection.

According to a second rule, the number of defect pixels as a proportion of the total defect area is to be brought to a minimum.

In each stored binary image, the defect pixels as a proportion of the total defect area are counted. The image with the fewest defect pixels is selected and is conveyed to the image processor/classification system.

Figure 4A:
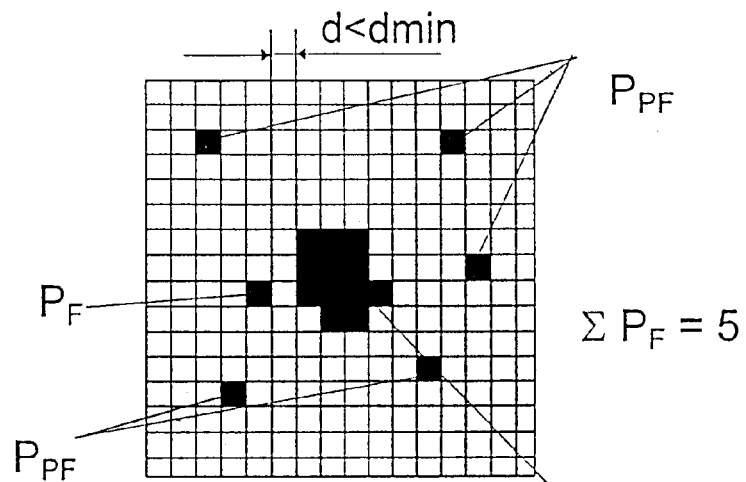
FIGS. 4a–4c show binary images of image fields of a defect region that are acquired with various focus settings in order to ascertain the number of pseudo-defect pixels.
Figure 4B:
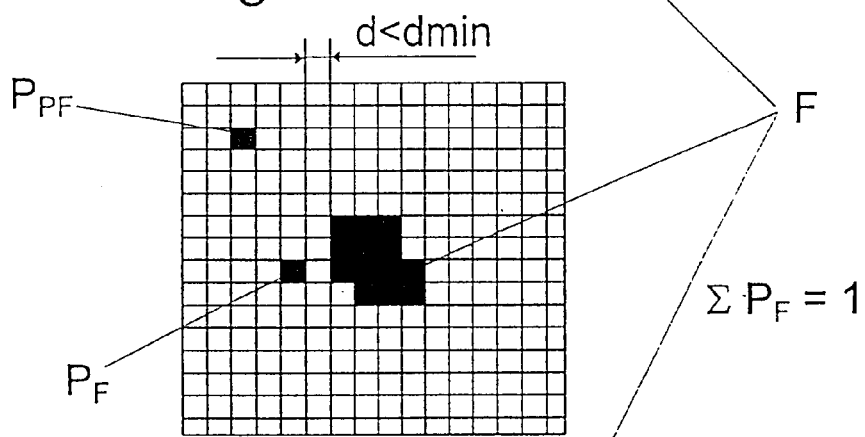
Figure 4C:
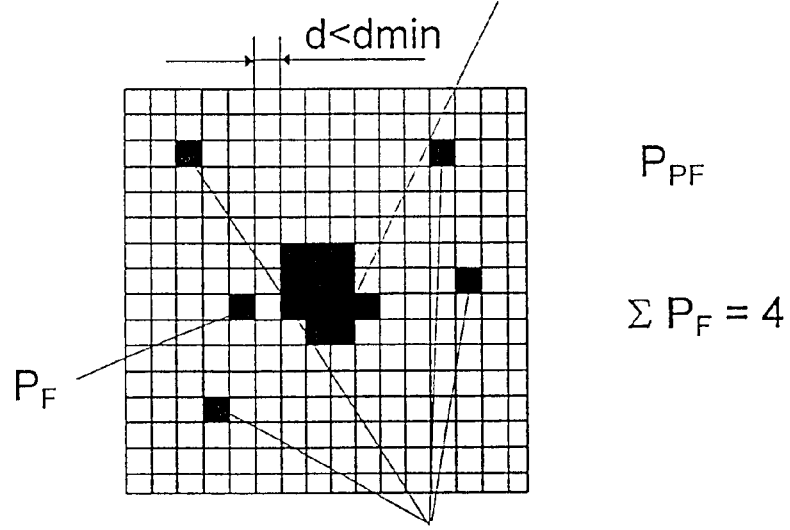

According to a third rule, which is illustrated in FIGS. 4a–4c, the number of pseudo-defect pixels is to be brought to a minimum.

Pseudo-defect pixels $P_{PF}$ are defect pixels that are not to be allocated to the actual defect F, defect F constituting the numerically greatest cohesive accumulation of defect pixels.

Those defect pixels $P_F$ that are at less than a minimum distance $d_{min}$ from the defect are also counted as part of it.

The pseudo-defect pixels $P_{PF}$ left over using this criterion are counted.

In the present example as shown in FIGS. 4a to 4c, in which a distance d to defect F of one pixel width is less than the minimum distance $d_{min}$, the resulting number of pseudo-defect pixels $P_{PF}$ is five in FIG. 4a, one in FIG. 4b, and four in FIG. 4c.

The binary image that has the fewest pseudo-defect pixels $P_{PF}$ (FIG. 4b) is selected for image processing and classification.

Lastly, according to a fourth rule, the defect with the greatest contrast is to be imaged.

The images acquired with CCD measurement system 14 via frame grabber 21 are processed in image processing unit 25 and subjected to a contrast maximization process.

A contrast maximization process is based on dividing the image fields into windows of, for example, 3×3 pixels. In each of these windows, the gray value of the central pixel is ascertained on a digital scale of 0 to 255, and the difference in terms of the gray values of its neighboring pixels is calculated. A mean is created from these differences. The gray value difference thus ascertained for each window is summed over the entire image field. The result is stored with the image field.

The process is repeated for each of the predefined focus settings.

The highest-contrast image field is the one with the maximum gray value difference, and is used for image processing and classification.

For the exemplary embodiments regarding focusing during inspection and defect classification, the fourth rule is the one predominantly used, although this does not signify any limitation on the usability of the other rules.

In order to carry out the method according to the present invention, for both inspection and defect classification it is first necessary to determine basic settings for the focus regulation system which on the one hand compensate for instrumental influences and on the other hand narrow down the search range for a focus setting referring to a subregion of the surfaces. For example, it is necessary to balance the optical focus measurement system 13, which operates in the infrared region, against CCD measurement system 14, which operates with visible light. Other disruptive influences are drifting and optical tolerances.

CCD measurement system 14 and the contrast program are used to select the highest-contrast image from an image sequence of a device-mounted test pattern, in the form of a checkerboard pattern, made with different preset values for the focus regulation system. The preset value for the focus regulation system belonging to that image constitutes the basic setting or basic offset OFFS_G.

For focusing during inspection, it is important whether the surface to be inspected is patterned or unpatterned.

An unpatterned surface is substantially free of reflectance fluctuations. Influences of pattern topology on the focus setting are insignificant.

The focusing system is adapted to the semiconductor wafer and, in particular, to defects on its unpatterned surface using a procedure in which, based on the basic setting OFFS_G of a selected defect, an image series is acquired using various preset values for the focus regulation system. The preset value at which the pseudo-defect rate is minimized as stated in the presentation of the object is determined by rule application in the form of the second rule.

For the inspection of patterned surfaces, it is necessary for the optical focus measurement system to be adapted to the wafer thickness and to the image content of the semiconductor wafer.

This is done on the basis of a reference region that corresponds to a subregion on the semiconductor wafer and can also be a chip or a portion of a chip.

The size of the reference region is determined by the fact that with the resulting adaptation of the optical focus measurement system in the form of the preset value of the focus regulation system, no defocusing occurs even in edge areas.

The reference region is selected using a method with which, at the locations of repeating height marks (marks that reproduce the height profile) and on the basis of the basic offset OFFS_G, the highest-contrast image is determined, by image processing for each location, from series of images each acquired with a different default setting of the focus regulation system.

Values for the distance between carrier plane E—E and reference plane B—B allocated in each case to the highest-contrast image yield a height profile of the semiconductor wafer. A flat region for which the height profile possesses the smallest height gradient is suitable as the reference region.

Within the reference region, an image series is in turn acquired with various default settings of the focus regulation system, at at least one selected position and on the basis of the basic offset value OFF_G. The preset value of the focus regulation system associated with the particular highest-contrast image ascertained by image processing is stored as the reference setting $OFFS\_ref_{xi,yi}$ as the reference basis for inspection, with its location coordinates (i for the X direction, j for the Y direction).

The region with preset values of the optical focusing measurement system is "learned" in accordance with the number of selected positions.

The device is now capable of inspecting regions comparable to the reference region, one image field at a time, with the goal of recognizing defects.

The regional setting comprises the wafer topology of the region. Pattern-dependent reflectance fluctuations generally do not have a disruptive effect on focusing, due to their repetitive nature.

If the reflection conditions differ in different regions despite having identical image contents, it is of course possible to compensate for this in the manner already described by acquiring an image series.

For defect classification as well, it is necessary to adapt the optical focus measurement system to the wafer thickness and the image content of the semiconductor wafer using a reference region. The reference region is selected in the same manner as for inspection. The essential selection criteria are flatness and freedom from defects.

In defect classification, it is moreover also necessary, for each wafer, to compensate for reflectance fluctuations on its surface.

For this purpose, an image series of a height mark is acquired at at least one location of the reference region, using the basic setting OFFS_G and using different preset values of the focus regulation system, and the highest-contrast image is selected by image processing. The associated focus setting OFFS_ref and the distance FP_ref between carrier plane E—E and reference plane B—B are stored as preset values for defect classification.

"Defect classification" means comparing the image content having a defect requiring classification to the image content of a reference image.

By setting the distance FP_ref of carrier plane E—E from reference plane B—B, the image content of interest in the reference region is acquired and stored as a reference image.

Using the default focus value OFFS_ref, an image series of the defect image is acquired using different optical focus settings, and image processing is used to select the highest-contrast image. The distance between carrier plane E—E and reference plane B—B associated with that image constitutes the setting for acquiring the defect image that is compared to the reference image for classification purposes.

A similar procedure is used for additional defect images.

What is claimed is:

1. A method for focusing on disk-shaped objects with patterned and unpatterned surfaces comprising the steps of:

imaging the patterned and unpatterned surfaces on a disk-shaped object for defect detection and defect classification;

utilizing various preset values of a focus regulation system to acquire an image sequence;

learning at least one preset value on the basis of the image sequence at least at one position in a substantially flat reference region of the surface of the disk-shaped object;

providing a regulated adjustment of a measurable distance from a carrier plane to a reference plane, wherein the carrier plane serves as a support for the disk-shaped object;

adjusting the distance by applying the at least one preset value, which is overlaid on the focus regulation system; and evaluating a focus state by an image processor according to at least one rule, and the at least one preset value to be ascertained therefrom.

2. The method as defined in claim 1, wherein the preset value is determined according to the image having a minimum number of defects identified by the image processor, wherein the preset value is used to adjust the distance.

3. The method as defined in claim 1, wherein the preset value is determined according to the image having a minimum number of defect pixels in proportion to the total defect area, wherein the preset value is used to adjust the distance.

4. The method as defined in claim 1, wherein the preset value is determined according to the image having a minimum number of pseudo-defect pixels identified by the image processor on the object surface, wherein the preset value is used to adjust the distance.

5. The method as defined in claim 1, wherein the preset value is determined according to a highest-contrast image, which is used to adjust the distance.

6. The method as defined in claim 5, wherein the preset value belongs to the image having a minimum number of pseudo-defect pixels and is used to establish a corrected distance.

7. The method as defined in claim 1, wherein the reference region is selected based on the lowest gradient of the height profile of the surface, which is to be determined by ascertaining the values of the distance from a carrier plane to a reference plane at locations of height marks located on the object surface, for the associated preset values of the focus regulation system and using at least one rule for the preset value.

8. The method as defined in claim 7, wherein during an inspection of the object surface in which defects are detected for one image field at a time, the preset value of the focus regulation system ascertained for the respective image field position is used for focusing.

9. The method as defined in claim 7, wherein for defect classification, in which an image that contains a defect to be classified is compared to a reference image, acquisition of the reference image is performed with the corrected distance from the carrier plane to the reference plane ascertained for the reference image position, and in order to acquire the image with the defects to be classified, the value of the distance from the carrier plane to the reference plane used for focus setting is the one belonging to the highest-contrast image of a series of images with the defect to be classified, the preset value of the focus regulation system that belongs to the image position being varied in steps in order to generate the image series.

* * * * *